United States Patent
Fornell et al.

(10) Patent No.: US 11,741,436 B2
(45) Date of Patent: Aug. 29, 2023

(54) APPOINTMENT OPTIMIZATION ENGINE

(71) Applicant: Shurpa, Inc., Chicago, IL (US)

(72) Inventors: Benjamin James Fornell, Chicago, IL (US); Brendan Stephen Doms, Chicago, IL (US)

(73) Assignee: Shurpa, Inc., Chicago, IL (US)

( * ) Notice: Subject to any disclaimer, the term of this patent is extended or adjusted under 35 U.S.C. 154(b) by 0 days.

(21) Appl. No.: 17/873,018

(22) Filed: Jul. 25, 2022

(65) Prior Publication Data

US 2022/0358468 A1  Nov. 10, 2022

Related U.S. Application Data

(63) Continuation of application No. 16/540,043, filed on Aug. 13, 2019, now Pat. No. 11,397,925, which is a
(Continued)

(51) Int. Cl.
*G06Q 10/1093* (2023.01)
*G06Q 50/30* (2012.01)
(Continued)

(52) U.S. Cl.
CPC ....... *G06Q 10/1095* (2013.01); *G01C 21/343* (2013.01); *G06F 9/541* (2013.01);
(Continued)

(58) Field of Classification Search
CPC ........ G06Q 10/00–50/00; G16H 10/00–70/00; G01C 1/00–25/00; G06F 1/00–21/00; G06N 3/00–20/00
(Continued)

(56) References Cited

U.S. PATENT DOCUMENTS 5,272,638 A    12/1993  Martin et al.
5,897,629 A *   4/1999  Shinagawa ............ G06N 3/126
                                                                706/13
(Continued)

FOREIGN PATENT DOCUMENTS

DE    19903548 A1    8/2000
EP     0797164 A1    9/1997
WO  2008083273 A2    7/2008

OTHER PUBLICATIONS

Govindan, Kannan, et al. "Two-echelon multiple-vehicle location-routing problem with time windows for optimization of sustainable supply chain network of perishable food." International Journal of Production Economics 152 (2014): 9-28. (Year: 2014).*
(Continued)

*Primary Examiner* — Alan S Miller
(74) *Attorney, Agent, or Firm* — Bookoff McAndrews, PLLC (57) ABSTRACT

An all-encompassing system for planning and optimizing scheduled delivery appointments (or attended deliveries) through the utilization of a software tool having two major constituents: an asynchronously operating background advanced, genetic route optimization algorithm and an algorithm-informed communication user interface (whether through digital, or even analog, pathways, such as, without limitation, SMS, email, IM, and the like, oral communications, or any other possible means of communication). Such a system employs the optimization algorithm to determine efficient routes for delivery services in response to selections from contacted customers via the communication user interface. In this manner, the system allows for an initial base route generation from a set population of responding customers and negotiation through the communication user interface for a delivery time in relation to such a route.
(Continued)

Subsequent responses are introduced in relation to the route in efficient manner by the algorithm as well.

20 Claims, 3 Drawing Sheets

Related U.S. Application Data continuation-in-part of application No. 16/115,554, filed on Aug. 28, 2018, now Pat. No. 10,380,536.

(51) Int. Cl.
*G06Q 10/047* (2023.01)
*G16H 40/20* (2018.01)
*G01C 21/34* (2006.01)
*G06Q 30/0204* (2023.01)
*G06N 3/126* (2023.01)
*G06F 9/54* (2006.01)
*G06Q 50/28* (2012.01)

(52) U.S. Cl.
CPC ............ *G06N 3/126* (2013.01); *G06Q 10/047* (2013.01); *G06Q 30/0205* (2013.01); *G06Q 50/28* (2013.01); *G06Q 50/30* (2013.01); *G16H 40/20* (2018.01)

(58) Field of Classification Search
USPC .................................................. 705/7.11–7.42
See application file for complete search history.

(56) References Cited

U.S. PATENT DOCUMENTS

| | | | |
|---|---|---|---|
| 9,741,011 B2* | 8/2017 | Beach-Drummond | G01S 19/38 |
| 2001/0047285 A1* | 11/2001 | Borders | G06Q 30/02 705/7.24 |
| 2003/0074471 A1* | 4/2003 | Anderson | H04L 69/329 709/224 |
| 2006/0235739 A1* | 10/2006 | Levis | G06Q 10/08 705/1.1 |
| 2007/0083410 A1* | 4/2007 | Hanna | G06Q 10/0833 705/336 |
| 2008/0114638 A1* | 5/2008 | Colliau | G06Q 10/1095 705/7.19 |
| 2009/0164236 A1 | 6/2009 | Gounares et al. | |
| 2010/0030811 A1* | 2/2010 | Ku | G06Q 30/06 705/26.1 |
| 2011/0231334 A1* | 9/2011 | Jindel | G06Q 10/08 705/335 |
| 2012/0185363 A1* | 7/2012 | Gilbert | G06Q 30/0641 705/27.1 |
| 2015/0295881 A1* | 10/2015 | Anderson | H04L 61/3015 709/245 |
| 2016/0042303 A1* | 2/2016 | Medina | G06Q 10/063114 705/5 |
| 2016/0171439 A1* | 6/2016 | Ladden | G06Q 10/083 705/340 |
| 2018/0121878 A1* | 5/2018 | Bostick | G06Q 10/08355 |

OTHER PUBLICATIONS

Wong, Richard T. "Vehicle routing for small package delivery and pickup services." The Vehicle Routing Problem: Latest Advances and New Challenges. Springer, Boston, MA, 2008. 475-485. (Year: 2008).*

Wang, Xiubin, and Amelia C. Regan. "Local truckload pickup and delivery with hard time window constraints." Transportation Research Part B: Methodological 36.2 (2002): 97-112. (Year: 2002).*

Ropke, Stefan, and David Pisinger. "An adaptive large neighborhood search heuristic for the pickup and delivery problem with time windows." Transportation science 40.4 (2006): 455-472. (Year: 2006).*

Nanry, William P., and J. Wesley Barnes. "Solving the pickup and delivery problem with time windows using reactive tabu search." Transportation Research Part B: Methodological 34.2 (2000): 107-121. (Year: 2000).*

* cited by examiner

APPOINTMENT OPTIMIZATION ENGINE

CROSS-REFERENCE TO CORRELATED APPLICATION

This application is a continuation of U.S. Non-Provisional patent application Ser. No. 16/540,043, field on Aug. 13, 2019, which is a continuation-in-part of U.S. Non-Provisional patent application Ser. No. 16/115,554, filed on Aug. 28, 2018, (now U.S. Pat. No. 10,380,536), the entirety of which are incorporated herein by reference for all purposes.

FIELD OF THE INVENTION

The present invention relates to an all-encompassing system for planning and optimizing scheduled delivery appointments (or attended deliveries) through the utilization of a software tool having two major constituents: an asynchronously operating background advanced, genetic route optimization algorithm and an algorithm-informed communication user interface (whether through digital, or even analog, pathways, such as, without limitation, SMS, email, IM, and the like, oral communications, or any other possible means of communication). Such a system employs the optimization algorithm to determine efficient routes for delivery services in response to selections from contacted customers via the communication user interface. In this manner, the system allows for an initial base route generation from a set population of responding customers and negotiation through the communication user interface for a delivery time in relation to such a route. Subsequent responses are introduced in relation to the route in efficient manner by the algorithm as well. Furthermore, the ability to utilize such a system for actual scheduled delivery of persons to appointments, coupled with relating the appointment time simultaneously, may be accomplished, as well.

BACKGROUND OF THE PRIOR ART

Scheduled delivery of services, packages, etc., has proven to be the bane of logistics functions for many years. The standard presentation of service providers, for example, of sending an attendant between the hours of, for example, 8 AM and 5 PM, and the like, has left many a customer frustrated and helpless as such a person becomes a "hostage" and required to await arrival at any time within a wide window. Likewise, package delivery has proven to be difficult as set times are rare to be offered, only dates, and such delivery to a non-present individual has led to many instances of externally placed packages being stolen and/or damaged.

Typical service provider activities are now scheduled and handled either by "warning" calls directly from the attending worker or through a dispatcher providing some basis of prior notification of arrival. Even so, however, such calls may come at a time when the customer is ill-prepared to receive such a visit or even with an emergency creating a delay on the customer end of the operation. In other words, even with such a wide window as an initial service offering, and a prior call to notify the customer that the service provider is "on the way" or planning on arriving within the next thirty minutes (as an example), the customer remains at the mercy of the servicer with little in the way of definitive determinations as to when such a delivery is expected.

This problem, as noted above, remains a distinct difficulty for all parties as the customer is forced to wait without any definitive (or even rough understanding) of the time such a service delivery is expected. The prior call merely shortens the time involved, but the window of expectation remains wide until the dispatcher or provider informs that delivery is in transit (hopefully). Such dispatch activities typically involve a spreadsheet with "on the fly" decisions as to where and when the next delivery should occur.

As alluded to, such deliveries are not limited to services, but goods as well. For instance, demand for large items (furniture, appliances, etc.) for risen as of late, but the delivery schedules for such activities are generally wasteful and poorly planned. For example, with a large truck, a number of large items may be included for a delivery operation. However, logistically, the best practice would seem to be to determine the most efficient route first and stock the truck appropriately with the first delivery at the nearest point of egress and all subsequent deliveries introduced further back, all in order to ensure the delivery person(s) can remove such goods in order of location involved. As it is, such considerations are generally not made until the last minute or the routes themselves are poorly planned (or both). It has not been uncommon that such scheduled goods deliveries are late from a planned time, or missed entirely due to logistical problems. As well, updating customers of planned delivery times are typically made via dispatch and by phone, leaving all parties at the mercy of availability of the parties involved and proper connections being made.

There is thus a significant need to provide a better customer experience with a system that utilizes more effective consumer interaction (through chatbot devices, for instance) and simplified and reliable negotiation and determination of delivery times and dates. To date, the only possible improvements involve, as one example, systems designed primarily to manage carrier capacity in terms of time and distance parameters and physical delivery vehicle capacity measurements, but still through a dispatcher individual. Another system utilizes a website to schedule a large item delivery through selecting carriers dependent upon geography and carrier load capacity, rather than route planning. Such prior and state of the art systems are significantly deficient as it concerns logistics for the delivery provider, particularly in terms of route planning, and fail to simultaneously provide reliable times to meet customer expectations (with pinpointed accuracy).

Additionally, the ability to schedule appointments is typically achieved through a call-in or on-line system with a written or filled in placement. Combined with transportation, however, has not been undertaken through any combination other than setting the scheduled appointment first and then requesting transport thereto. For instance, typical health care or like medical appointments are standardly handled as above; basically, submit a request and then an appointment time is filled, followed by the ability to then request transportation for such a purpose to and from the appointment. This is quite an inefficient operation as the overall approach relies more on appointment times, rather than any combination of that plus a transport possibility. Such a correlation may provide far improved operations, but, to date, nothing has been indicated combining the two activities, and particularly not as it concerns an overall effective procedure related to geo-location issues primarily. In any event, the state of the art is lacking any such potential.

As it concerns all of these geo-location based activities and operations, the following disclosure remedies such shortcomings.

Advantages and Summary of the Invention

One distinct advantage of the present disclosure is the ability to provide a complete delivery (whether a service or a good) schedule planning and optimization platform with customer negotiation capabilities. Another advantage is the ability to provide such a delivery platform through an initial geographically segregated delivery route developed in response to direct customer input and requests with subsequent and completed route development upon receipt of subsequent customer input past an initial population within a set timeframe and geographical region. Additionally, the disclosure provides an interface for simplified communication and negotiation between service provider/carrier and consumer to maximize effectiveness and reliability of delivery time results. An additional advantage, particularly as it pertains to appointments and transportation scheduling (delivery of persons or goods), is the ability to provide complete transportation and appointments operations in one request with an efficient overall scheme for both delivery and return.

Accordingly, this invention encompasses a delivery scheduling system for effectively and efficiently generating delivery routes and schedules between a delivery client and a plurality of delivery customers, said system comprising a central functionality hub including a route optimization algorithm and at least four other sub-systems directly accessible to said central functionality hub, said sub-systems comprising a) at least one geolocation server; b) at least one routing server; c) at least one external communication user interface component for communication between said plurality of delivery customers and said central functionality hub algorithm; and d) at least one API for communication between a delivery client and said central functionality hub route optimization algorithm server; wherein said at least one geolocation server stores addresses for said plurality of delivery customers, wherein said at least one API acts as a conduit for transmitting delivery order requests regarding said plurality of delivery customers from said delivery client to said main server hub algorithm, wherein said at least one external communication user interface component acts as a conduit for said central functionality hub algorithm to request and receive delivery time requests within a certain time window from said plurality of delivery customers, wherein said central functionality hub algorithm correlates received delivery time requests from at least a population of said plurality of delivery customers with addresses for the same from said geolocation server in order to generate possible routes for delivery associated with such received delivery customer time requests with said possible routes compared internally to meet a certain viability score level with the optimal result chosen and placed on said routing server as an initial framework, wherein said central functionality hub algorithm provides a confirmation of a narrow delivery window to responsive delivery customers upon initial framework route generation with the potential for any responsive delivery customer to request modification of such a narrow delivery window confirmation, wherein said central functionality hub provides subsequent requests to non-responsive delivery customers in order to update said initial route framework with subsequent replies of requested narrow delivery time windows and providing confirmations thereof as said delivery route is updated in relation to such subsequent responses and/or said requests for modifications from confirmed delivery customers. Such a system may be utilized in relation to goods delivery activities or service provisions, either in terms of allowing a negotiated narrow delivery window that allows for greater certainty for the delivery customer or greater efficiencies for the delivery client. As an overall method, such would utilize the system as described with the following steps:

i) said delivery client transmits through said API a plurality of orders to said central functionality hub algorithm including delivery customer addresses, delivery dates, delivery promised times, and customer mobile phone numbers for each of said plurality of customers associated with said plurality of orders for said delivery date;

ii) said central functionality hub algorithm generates communications with each of said plurality of customers requesting a response from each customer indicating a selected delivery time window and alternatives thereof from an available list on said delivery date, wherein said communications are provided via said at least one external communication user interface component;

iii) a population of said plurality of customers provides responses with selected delivery time windows and alternatives thereof to said central functionality hub request, wherein a predetermined number of responses below the full number of said plurality of customers allows for generation of pre-routes for delivery purposes associated with said plurality of orders by said central functionality hub algorithm, wherein said pre-route result is produced through a consideration of multiple variables associated with the addresses of each of said population of plurality of delivery customers through accessing of said geolocation server, the requested time windows from each of said population, and delivery client capabilities and desired efficiencies, wherein upon generation of said pre-route result, said central functionality hub algorithm generates confirmations for transmission through said at least one external communication user interface component notifying said responding customers of accepted narrow delivery time windows within the requested time periods indicated within said customer requests, and the ability for said confirmed customers to request modification thereof, if desired;

iv) wherein said central functionality hub algorithm continues to seek responses from the group of customers that have not provided such replies prior to pre-route result generation, wherein such algorithm requests include available narrow delivery time windows in relation to said already generated pre-route results and already determined delivery times for such confirmed customers; wherein upon receipt of such responses said central functionality hub algorithm generates pre-route adjustments to accommodate such subsequent customer requests in order of receipt without modifying the confirmed customer delivery time periods, wherein confirmations are generated and communicated through said at least one external communication user interface component to said subsequently responding customers, wherein said confirmations notifying such subsequently responding customers of accepted narrow delivery times within the adjusted pre-route results, and the ability for said subsequently confirmed customers to request modification thereof, if desired, wherein said continued requests for responses from said central functionality hub algorithm continue until all eligible delivery customers within said plurality related to said plurality of orders have been provided with a narrow delivery time window;

v) said central functionality hub algorithm then generating a final route with all delivery times and addresses determined and transmitting the same to said routing server for utilization by said delivery client; and vi) said delivery client then providing delivery of said plurality of orders to said correlated plurality of delivery customers in alignment with said final generated route.

Additionally, such a disclosure may encompass appointment and transportation delivery scheduling system for effectively and efficiently generating time and date appointments and related transportation delivery routes between an appointment customer and a plurality of appointment clients/patients, said system comprising a central functionality hub including a route optimization algorithm and at least four other sub-systems directly accessible to said central functionality hub, said sub-systems comprising:

a) at least one geolocation server;

b) at least one routing server;

c) at least one external communication user interface component for communication between said plurality of delivery customers and said central functionality hub algorithm; and d) at least one API for communication between a delivery client and said central functionality hub route optimization algorithm server;

wherein said at least one geolocation server stores addresses for said plurality of appointment clients/patients, wherein said at least one API acts as a conduit for transmitting appointment requests from said plurality of appointment clients/patients regarding said appointment client to said main server hub algorithm, wherein said at least one external communication user interface component acts as a conduit for said central functionality hub algorithm to request and receive appointment requests within a certain time window from said plurality of appointment clients/patients, wherein said central functionality hub algorithm correlates received appointment requests from at least a population of said plurality of appointment clients/patients with addresses for the same from said geolocation server in order to generate possible routes for transportation therefrom such addresses to said appointment client and couple such routes with open appointment times available at said appointment client, with such generated routes and combined appointment times compared internally to meet a certain viability score level with the optimal result chosen and placed on said routing server as an initial framework, wherein said central functionality hub provides subsequent requests to nonresponsive appointment clients/patients in order to update said initial route framework with subsequent replies of requested narrow delivery time windows and providing confirmations thereof as said transportation route and related appointment times is completed.

In this manner, the central functionality hub algorithm (also referred to herein as the route optimization algorithm) allows for a number of different automated actions that are impossible to undertake through human interaction and is not simply just a replacement for human activity as a result. Such an optimization operation relies upon the initial receipt and weighing of different criteria and variables associated with a variety, if not myriad, pieces of information. This algorithm thus may utilize information for an entire fleet of delivery vehicles in order to generate routes over a significant geographical area over a certain time period (an hour, a day, a week, etc.) or may be limited to a single delivery provider, truck, etc., over a limited time duration (but will multiple delivery requests). The geographical considerations are of importance, certainly, as the need to provide fuel efficiency, at least, and thus to determine a suitable route associated with a population of delivery customers within a certain region may be viewed as of a higher weighed variable overall. The time windows for such deliveries, in relation to those as requested by the initial population of delivery customers for the pre-route (framework) generated results also factor heavily within this consideration. Other issues, as noted herein, may include the types of vehicles available, expected delays in traffic patterns, and the like. In any event, the algorithm receives such information, compiles the same, and generates any number of possible routes for comparison with historical data pertaining to typical routes and efficiencies understood thereby, or, alternatively, and if historical data is not present, through a general consideration of expectations through understood conditions of the same type. As it is, the algorithm will generate thousands of different routes, weigh the benefits of each in comparison with all of the others, and generate a score through a mathematical approach to determine the most effective and efficient pre-route possible, all within a time frame of between a few minutes to as little as a few seconds (if not lower). Again, such a determination would be impossible through human interaction. The initial population pre-route (framework) is then used as a base with set time windows for such initially responding delivery customers (and thus set routes associated with such set time windows for such customers). The algorithm then receives further delivery customer responses to "fill in" the empty time windows without changing those already in place for the initial responders (basically allowing for an early response reward system, in essence) while taking into consideration the pre-route configuration and geographic locations of such subsequent requesting customers in relation to such persons' selected delivery time windows as well. Of course, with the initial population of delivery customers already provided with set delivery time windows, the subsequent requests sent by the algorithm through the chatbot interface to the other customers would have far fewer available time windows, with each successive response with more available possibilities and each subsequent reply with fewer and fewer delivery time window options. The algorithm thus generates a final route for the delivery client once all responses and delivery customer requests are received and assessed.

Thus, the route optimization algorithm functions in a manner that has not been undertaken within this industry. In particular, the ability to assess direct customer requests through a communication user platform (such as, without limitation, a computerized, digital, or analog, for that matter, platform, including an SMS format, email system, instant messaging, etc., oral communications, such as by phone, voice messaging, and the like, or even a hybrid, such as through a SIRI, ALEXA, or other like communication base device, and the like) and ostensibly via the utilization of a chatbot interface permits a facilitated operation that allows for smooth operations and effective route generations quickly and decisively. In this situation, then, the algorithm basically receives a request for a delivery (whether a service or a good, as explained above) from a client (courier/carrier) via an API (electronically, in other words). Such a delivery request includes specific information including, without limitation, the customer delivery address, the delivery request date, a time window for the requested appointment/delivery time, and the customer phone number, particularly associated with a chatbot and accessible through a communication user platform (again, without limitation, formats such as SMS, email, IM, ALEXA, telephone messaging, in-person voice communications, and the like). This request is collected with others from different customers and assessed in terms of a timeframe (such as within a 24-hour period, for example) as to create a pool of customer delivery requests that are then assessed in relation to geography considerations through the algorithm itself. The algorithm then generates a response to each requesting customer as to specifically requested times for delivery/appointment in order to allow for customer input to create a pre-routing result in relation to the requested deliveries/appointments within the timeframe at issue. Such an initial time request allows for the algorithm to generate an initial framework route as a starting point (whether for an individual provider/carrier, or perhaps multiples on the same date, or at least within the same time window for such multiple customers). Such a framework (pre-) route is generated in relation to a pre-determined population of customer responses with full information for geographic assessments. In other words, for example, upon receipt of responses from an initial 25% of all customer requests for delivery/appointment within a specific time window, the algorithm utilizes a number of different variables to generate multiple possible route results with continued assessment as to optimal considerations in relation to previous and similar generations of routes from past operations. Such variables include, without limitation, total distance the client needs to reach all destinations and return, total time needed for full completion of delivery activities, time on site for each delivery/appointment, average distance between delivery stops, average time between delivery stops, average and maximum speeds permitted for driving, the total number and type of client delivery vehicles available for such purposes within the time window itself, any time allowed for early delivery/appointment, any time allowed for late delivery/appointment, and overall courier/carrier entity utilization within the time window. The algorithm is programmed to assess at least these concerns, and with weighted properties, potentially, included with each such variable (for instance, if total distance is considered paramount due to fuel costs, the algorithm may weigh such a variable as higher than others) the algorithm may generate a mathematical or other like "score" for each pre-route possibility, ultimately comparing such scores and generating a final result based upon the initial customer population responses up to the initial threshold (again, such as, without limitation, 25% of the total requests provided). With this pre-route in place, and the initial population (again, as an example, the first 25% responding customers; of course, such a number may be higher or lower, although for best results the number should remain below 50%, preferably at most about 35%, more preferably at most 30%, and most preferably at most 25%) of responding customers provided not just with a place within the pre-route, but with a definitive set time for delivery/appointment with a confirmation message through the API. Of course, until the threshold minimum of customer responses is received, the system will continue to request such responses in order to generate the pre-route from which further arrangements are introduced.

Thus, the system begins the overall operation with such data ingestion transmitted from the client delivery provider and including the complete customer address with cardinal street direction and suffix, customer name, and customer cell phone number, ostensibly, again, for communication user platform chatbot communication capability. This may be accomplished through the aforementioned API interface or through, if desired, an upload (such as through a website or other CSV possibility). The system then engages a logic tree program via communication user platform interactions (SMS, email, IM, voice, ALEXA, etc.) with each indicated customer to allow for the actual receipt of delivery time requests. Such interactions include, as merely examples, initial messages indicating the courier/carrier (i.e., client or merchant) involved, with the options to track a delivery, an indication of proof of delivery, the ability to update any delivery instructions/requests, or even contact information for support issues. Such sub-menus thus allow for direct contact via the communication user platform (SMS, email, IM, voice, ALEXA, etc.) pathway for communication purposes with such specific concerns.

The scheduling process itself begins automatically once an order is actually placed and all data relating thereto is received. With information pertaining to the requesting customer already in place, corresponding data between such information and the order thus leads to correlation of the parties involved and the overall system thus is primed to send out delivery time requests within a specific time window. With such a plurality of customers within a time window (as an example), the system (algorithm) assesses such eligible deliveries for communication capabilities with such customers. Upon conclusion that such individuals/entities are suitable for such a routing optimization operation, the algorithm generates a request (through the chatbot) indicating that the delivery of such goods and/or services are ready to be delivered in the near future, thereby eliciting a response as to a requested delivery time, possibly with a primary time and other alternatives, or within a much narrower window than over the course of a full day. The customer may then select such a time (or times) or may be provided with a number of options in this respect from which a specific time may be chosen (corresponding with the provisions, for instance, in relation to the service level agreement governing the activity/sale). In any event, once the customer provides such a response, particularly if within the threshold minimum needed for algorithm pre-route generation capabilities, the algorithm compiles such received responses, assesses the already correlated addresses for each delivery, and generates multiple possible pre-routes for comparison with weighed variables to calculate individual pre-route values to ultimately determine the best pre-route result(s) (since this may be for more than one delivery vehicle or service individual, as the overall system allows for overall business capabilities and efficiencies, not just for single delivery persons and/or vehicles) on which all further customer responses will then be considered for entry therein. Thus, although the threshold minimum of responses sets the pre-route(s), of course the system will continue to request responses from the other customers for complete route generation, both in terms of geography and time constraints. As such, the initial pre-route generated should be viewed as a framework with the responding customers provided with their requested times within such a framework, and the remaining responding customers provided with delivery times that fit within the framework and as best to meet requested times after such a pre-route has been set. To that end, it should be understood that the pre-route result (framework) will be continuously updated as such subsequent responses are received. As such, the pre-route (framework) is considered a temporary situation based upon the geographical considerations (addresses) of existing scheduled deliveries. With the subsequent responses, then, the planning process is updated and the algorithm continues to generate comparative generations of routes with scores to assess the best updated result in that manner. In this way, the framework is set as the initial route with the remaining deliveries "filled in" for efficiencies, utilizing the most up-to-date information with each such algorithm routing optimization result. It should be well understood by the ordinarily skilled artisan that although it is desirable and at times intended that such customer communications for route creation (and thereafter for completing routes after initial route creation) are processed in relation to the time sent and time received by the algorithm within the central functionality hub, it is well within the realm of possibility that such communications may be delayed in terms of being sent and/or being received through any type of anomaly or communication interference. Thus, it is well within the scope of the disclosure herein that such an asynchronous result will still provide the proper foundation for route creation and completion.

In this overall system, then, there is made available a way for customers to effectively negotiate for more definitive, if smaller (shorter), delivery windows, while the courier/carrier can better plan for greater effectiveness and efficiency with their own operations. The algorithm can assess delivery times in relation to a number of different routes within a geographical region, for example, placing the customer within a time window that is narrowed for maximum effect for both customer and/or client parties. Such a negotiation capability has not been made available, particularly with the utilization of a chatbot operation, within the courier/carrier industries of concern. For instance, then, if a courier/carrier had 100 scheduled deliveries in a given day, the system would upload the 100 customer addresses and cell phone numbers, initially, and then initiate a communication user platform-based (i.e., SMS, email, IM, voice, ALEXA, as non-limiting examples, again) message to all such customers via the chatbot. Since responses will not typically be generated simultaneously, such replies will trickle in, most likely, thus allowing for a merit-based system, if you will, as the earliest responders will be provided preference as to meeting requested time windows. Once, then, a pre-set population has responded (again, such as a 25% threshold, thus, here, the first 25 responses), the algorithm is able to take the geographical information for each early response and generate, as noted above, the pre-route with geography and times provided with a temporary framework. The earlier responders are thus allowed, as noted above, a more certain, narrower, time window for delivery purposes and upon receipt of further replies in this respect, the algorithm is able to reassess the overall route framework(s) for each delivery person/vehicle and fewer possible choices for delivery times are offered for such later responders. Thus, as each subsequent customer response is provided, the available delivery times are more limited, up to the final available slot which may be a single time (possibly more) but at least at a potentially specific measure for such a delivery activity, rather than a wide-open window of possibility. This system thus allows the courier/carrier a means to assure delivery in relation to a number of previously considered and assessed variables (thus allowing for greater efficiencies overall and expectedly happier customers, as well) and the customer the ability to limit her or his (or its) time needed to be present for such a delivery operation. This ability to negotiate through the chatbot device further accords greater flexibility and reliability for both parties, particularly as it can provide a simplified manner of requesting not only initial scheduling, but also requests for rescheduling (if the routed time is unacceptable or difficult to meet), provisions and/or changes in instructions to the courier/carrier, and even just direct support contact. The routing optimization server (of the central functionality hub) communicates directly in this manner with the chatbot, allowing for any number of communication user platforms for such a purpose, including, without limitation, conversational, digital, analog, voice, hybrid, etc., communications, including, without limitation, SMS, email, IM, voice messaging, and the like, thereby, again, facilitating the overall communication capabilities between all parties involved.

As alluded to above, the central functionality hub (which may be provided in terms of a base server, a cloud server, or any other type of device and/or system that provides such a central functionality presence and capability) (again, here including the routing optimization server and algorithm) includes four main sub-systems to undertake and successfully implement this overall delivery set-up (it would be well understood by the ordinarily skilled artisan that such sub-systems may be provided within the central functionality hub as separate programs and/or devices, therein, or may be combined within merged or coexisting programs and/or devices in any manner). The central functionality hub receives the initial request of an order that will require delivery in some way, accompanied by the customer identifying/locating/communicating information. Such is retained within the central functionality hub (algorithm) until activation through receipt of a response relating to the initial delivery request itself. Thus, again, upon notification that a delivery is to be undertaken, possibly as it concerns a number within a certain time frame, the central functionality hub (algorithm) determines if a sufficient amount of information has been received to generate a pre-route for all such time-related deliveries. If the system has sufficient information (i.e., the threshold minimum has responded to the initial request), then the algorithm generates the pre-route as noted above. If not, then the algorithm utilizes the chatbot component to communicate with each delivery customer to request the information pertaining to initial delivery questions. Once the initial threshold number has responded, the system (algorithm) can generate the pre-route(s) as noted previously. The server (hub) can then generate a confirmation for each accepted delivery customer, notifying of the set narrow window of delivery as well as allowing for the customer to change such a result and/or communicate with the carrier/courier as needed and if desired for whatever reason. If a change is requested, the central functionality hub (algorithm) considers further geographical options and assesses the same for a pre-route framework in an updated fashion, whether that same day, within the same route, or within a different route, or a different date, if needed, all through the communication utilization of the chatbot feature. Thus, the customer has the ability to modify a requested/set delivery time and date after such has been generated within the system, allowing for greater customer acceptance and pleasantness. As well, such a possibility further allows the courier/carrier the ability to effectively operate with greater efficiencies as all such routing optimization possibilities are made through a continuously updated algorithm program that considers thousands, if not more, route possibilities and weighs and scores them to accord the most reliable and robust result with set times and dates for customers (for greater certainty as to delivery operations) and considering all other variables needed to guarantee such desirable efficiencies.

The central functionality hub (i.e., routing optimization server) includes, as another sub-system, a geolocation server that correlates addresses as inputted in full and assigned from each customer from whom an order has been received. Such a geolocation server thus allows for quick and easy correlation between an address and a route possibility for the algorithm to undertake, particularly upon receipt of a plurality of requests (including, of course, the initial threshold population for pre-route framework generation and ultimately the final route through receipt of all eligible delivery customer responses to requests from the algorithm through the chatbot). The central functionality hub also includes a routing server onto which the generated pre-route framework is initially placed and updated regularly as the algorithm receives more and more customer responses ultimately leading to a final route for utilization by the delivery client with the plurality of orders within that specific date and geographical range. Again, as noted above, it is well understood by the ordinarily skilled artisan that the geolocation and routing server sub-systems may be provided as a single program and/or device within the central functionality hub, if desired.

Such an algorithm may be undertaken through any type of software language, as would be well understood by the ordinarily skilled artisan. Certainly, code language ranging from C, C+, C++, Ruby on Rails, Python, and the like, may be employed for such a purpose. The API is accessible in any standard manner, whether through an app or otherwise via a computer-controlled system and/or environment. The geolocation and routing server may be similarly coded and handled as above, as well, with all such components available through remote access capability, via different methods, including, but not limited to, 3/4G, WiFi, Bluetooth, USB and other cable type connections and software applications, as desired. Lastly, the chatbot component allowing for facilitated customer communications via any type of communication user platform are well understood by the ordinarily skilled artisan, as well.

Furthermore, such a system (and method) may be provided as a standalone system for access by a delivery client through an API, thus allowing for multiple delivery clients to utilize the same system (and method) from the same source on a subscription or like basis. The mobile phone numbers provided with such order data allow from the system to communicate via the chatbot with such customers, as well, thus providing a simplified, yet highly automated, platform for delivery scheduling optimizations.

As it concerns the appointment optimization alternative, the system basically undertakes requests from appointment clients/patients (whether for medical, goods delivery, or any other like appointment necessity) as just a request and sets up a schedule based upon the location of each requesting client/patient in relation to any open appointment time and date for such a purpose. Certainly, such a medically based operation would be on a non-emergency basis, with the type of medical professional (herein referred to as appointment customer, encompassing any such delivery/scheduled appointment customer in this regard) or health care professional of any type, ranging from internal medicine, to psychiatric medicine, podiatry, chiropractic, family medicine, etc., the list covers any such medical possibility. As well, such may include clinics, hospitals (including, without limitation, Veterans' Administration hospitals), and any other type of location/office for such a medical purpose. With this alternative system, then, the appointment clients/patients for a certain appointment customer (or customers) send a request for aid in scheduling an appointment that combines with a request for transportation aid to and from such a location. The system basically receives the request (through an API, data upload, or manual entry, at least), such information including the request as well as, in any combination, the client/patient's physical location, possible desired date and/or time of appointment (or a range thereof; generally such can be more easily arranged through the geo-location capabilities in relation to transportation possibilities; as this is a non-emergency consideration, it should be understood that basing such scheduling on the facilitation of transportation will be acceptable; additionally, the ability to simply request time due to daily availability may be acceptable as well), a pick-up location (if not the requestor client/patient's home, and thus a different one from within the system's memory), and, if needed, appointment client/patient contact information. From such an initial request, the system thus, through a hub algorithm, generates an initial batch of routes that adheres to the initial request criteria (geo-location from requestor location to appointment customer location, primarily). From this, an initial appointment date and time is also created for each appointment client/patient that is then assigned, particularly as it relies upon not only a scheduling placement but the routing for transportation viability, as well. Such can then, as with the first alternative described above, be continually updated as to routing with more requests being made through the system until the cutoff time is met for a complete schedule, regarding both the appointment time and date and pick-up time (drop-off at the requestor location may not be possible due to, of course, overruns at the appointment customer in terms of other appointments). With this alternative, then, there is available the coupling of both providing a time and date for an appointment and the necessary transportation to and from such an appointment on a timely basis. As certain clients/patients require help as it concerns transportation (cannot drive, does not have family or help for such a purpose, etc.), as well as the benefit of matching, as best possible, the delivery of such clients/patients to appointments timewise, such aids in the reduction of possible fears and distractions of not only obtaining appointments to begin with, but also allowing for such timely travel to and from such an activity. Certainly, there are many difficulties for certain parts of the population (elderly, handicapped, etc.) in meeting such health care necessities, particularly as they concern the appointments initially and further the transportation availabilities, particularly as it would potentially pertain to arrival and departure therefrom at reasonable times, this system would be of great importance and facility. Such is described below, as well.

DETAILED DESCRIPTION OF THE DRAWINGS AND PREFERRED EMBODIMENTS

Without any intention of limiting the scope of the inventive system/device/method, the drawings described herein provide but one embodiment herein. Various modifications and different configurations of such a system/device/method may be employed without deviating from the scope and basis of the present invention.

Figure 1:
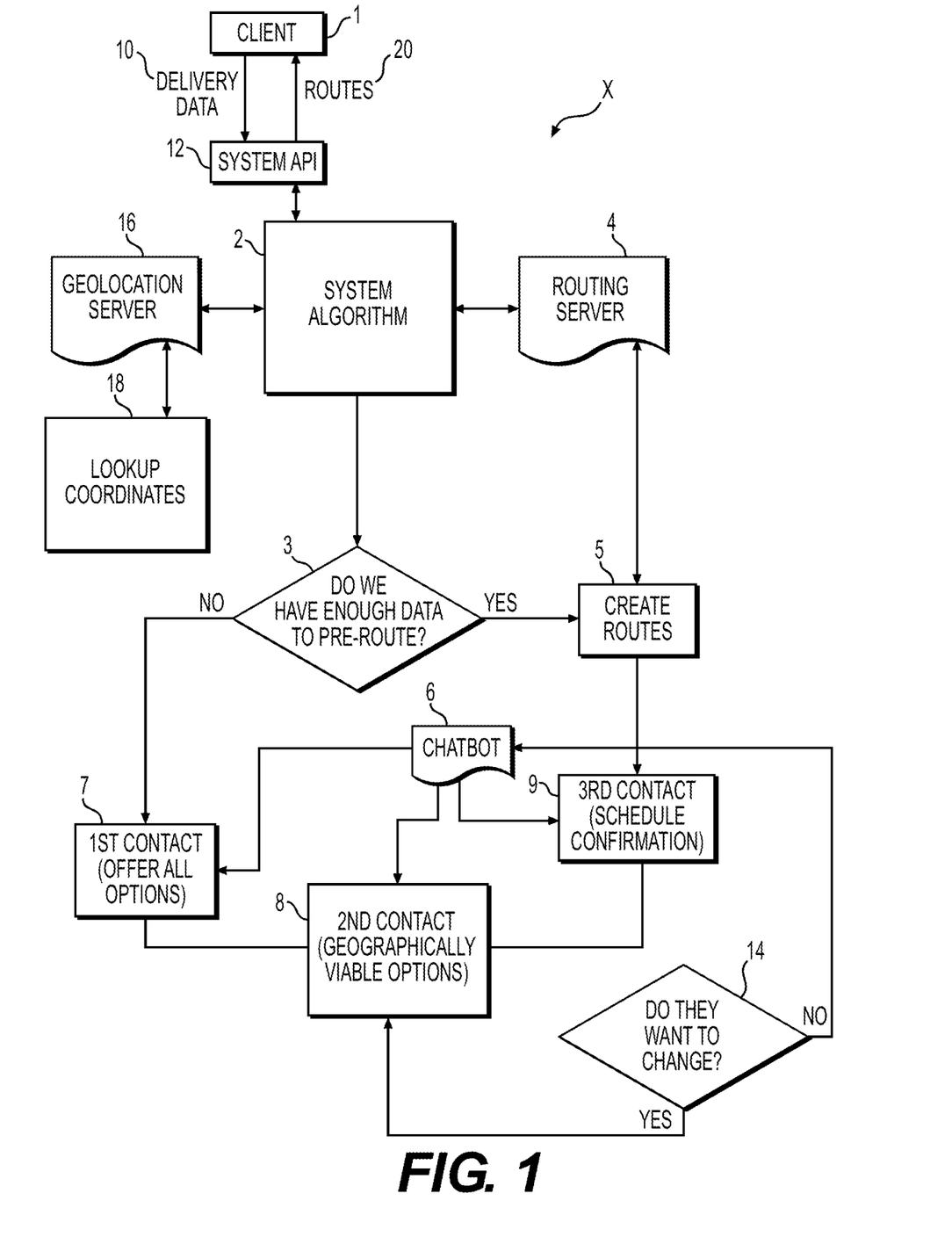
FIG. 1 depicts a flow diagram of a potentially preferred embodiment of the system and method of delivery scheduling as described herein.

FIG. 1 depicts a flow diagram of the overall system and method as a potentially particularly preferred version thereof. In this depiction, a delivery client 1 provides delivery data 10 through the API interface 12 to the main server hub algorithm 2. Such data 10 includes a list of orders from a plurality of customers, including addresses of each, mobile phone numbers of each, the date of delivery for each, and an initial delivery window provided for each, at least. The algorithm 2 takes such information determines if such a transmission from the delivery client 1 is sufficient to generate a pre-route 3 for such a request of deliveries of such a plurality of orders. If such is sufficient (i.e., all information received provided enough data to allow for time windows to be established, such as if the initial transmission included selected times from the delivery client for each customer, and if all addresses are provided for a geographic consideration to be made for a pre-route assessment to be made, as well), then the algorithm 2 generates a pre-route 5 for storage on the routing server 4. Such considerations include accessing the geolocation server 16 for specific coordinates 18 of each address to aid in overall assessments, along with aforementioned criteria and variables (time windows, capabilities of the delivery client, and the like). Thereafter, the algorithm 2 sends responses to any customers not providing sufficient information for further route generating considerations through the chatbot 6 seeking a selected time window from each such customer 8 with subsequent receipt thereof allowing for updating routes 5 and sending the same to the routing server 4. The algorithm 2 provides confirmation to all responsive customers with the ability to change any selected time windows thereafter 14, if desired. Once the final customer has responded to the algorithm 2 through the chatbot 6, the final route is generated, stored within the routing server 5, and transferred 20 from the main hub server 2 to the delivery client 1 through the API. The delivery client 1 may then utilize the full generated route to undertake effective and efficient delivery activities on the delivery date in question (or at least within the time period associated with all such orders sent by delivery client 1 to the algorithm 2).

Figure 2:
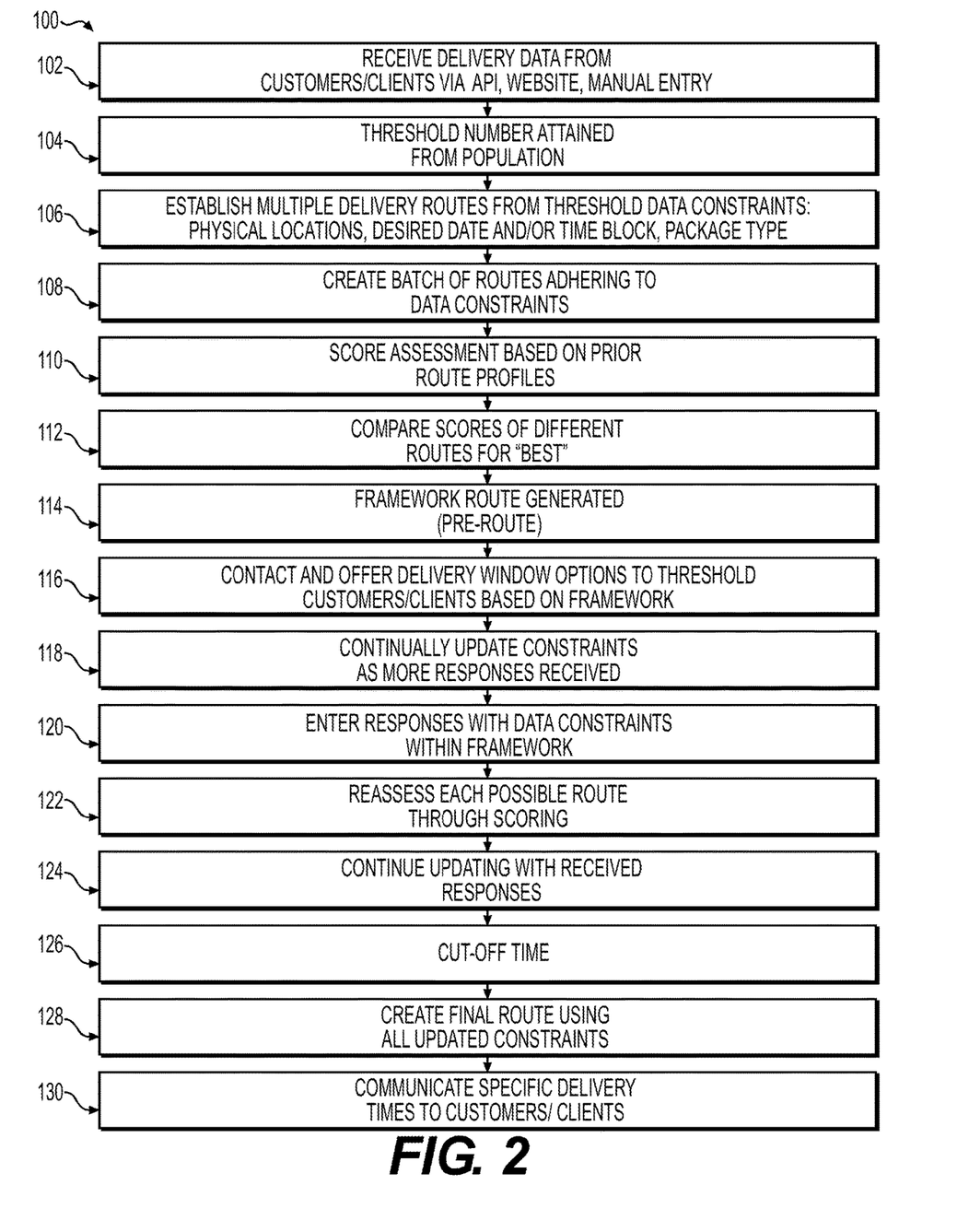
FIG. 2 depicts a flow diagram of a potentially preferred embodiment of the algorithm utilized within the system and method of delivery scheduling as described herein.

FIG. 2 depicts the route optimization algorithm as described above in a flow chart. Such an algorithm 100 receives, through an API, website, or other type of entry of information 102, delivery data 104 from an initial population of customers/clients in relation to a data constraint, including, without limitation, physical location, specific date of delivery, time block, package type, or other criteria/criterium 104. The initial threshold for pre-route generation is sought (again, as noted above, any percentage of the full population for a set delivery set, such as 25%, 30%, etc.) and, upon attainment of such a number 106, the algorithm compiles multiple routes in relation to data constraints 108, then assesses scores in relation to each generated route (in relation to prior routing profiles stored therein) 110, compares such assessment scores for the best pre-route for efficiency and effectiveness 112, generates a framework route 114 in relation to the best score in such a situation, and offers delivery window options to threshold customers/clients based on optimal route results 116. The algorithm then awaits the remainder of responses from the overall delivery population 118 and inserts each response in order of receipt within the framework 120 for continuous assessments and scoring for generation of further updated delivery routes 122 and updated results in relation to further response receipts and possible requests for modifications from earlier scheduled customers/clients 124, until final cut-off time is reached 126. The final route is then generated in response to completed updates and customer/client responses 128 and adopted within the overall system thereafter with final communication to customers/clients of delivery times 130. Thus, the route optimization algorithm 100 provides a continuously generating/updating component of the overall method to receive chronologically provided responses to requests for scheduling messages within an overall population of customer/clients for a delivery set, all within an initial pre-route framework that is then filled in subsequently thereto.

Figure 3:
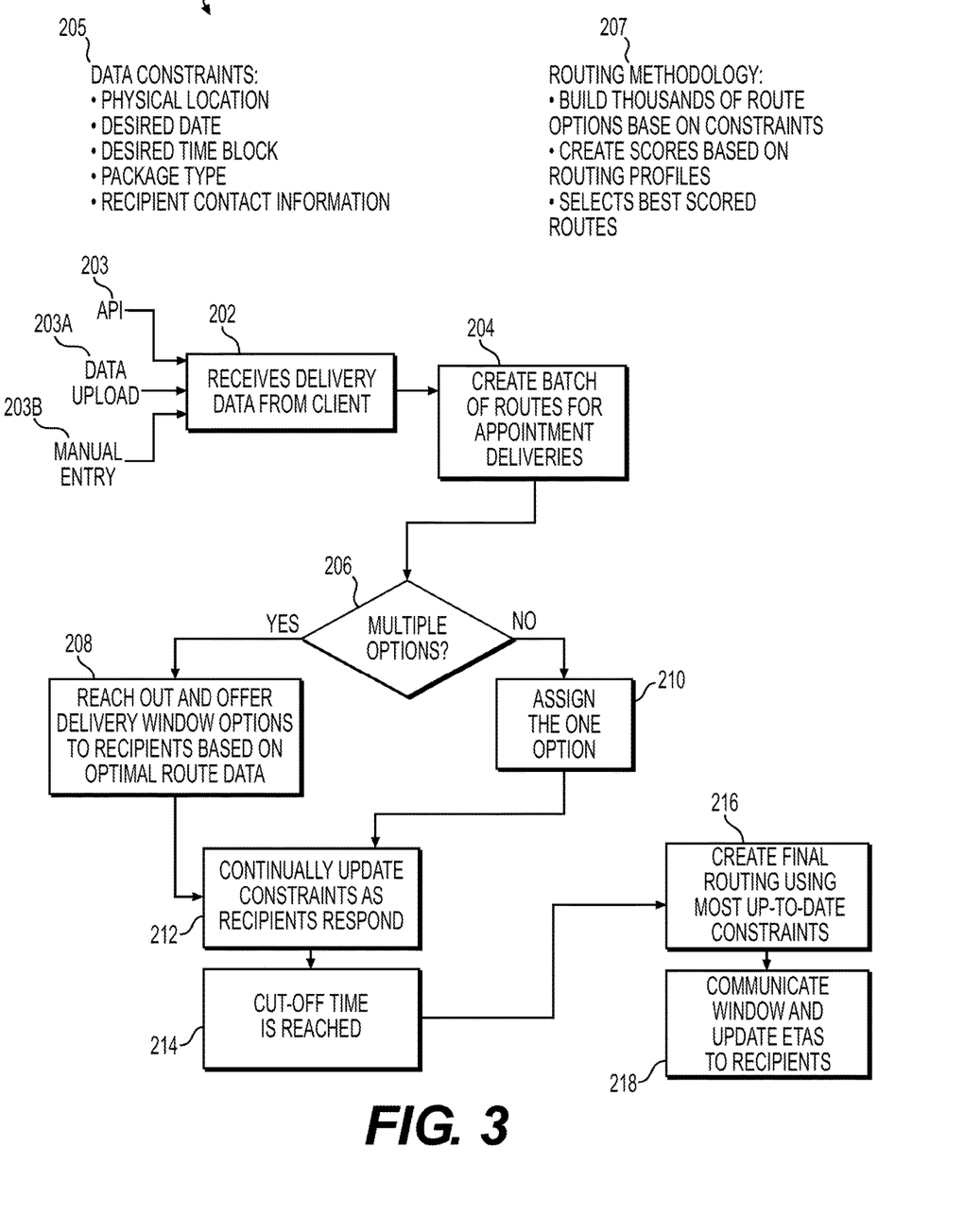
FIG. 3 depicts a flow diagram of a potentially preferred embodiment of the alternative appointment/transportation scheduling system and method thereof as described herein.

FIG. 3 depicts the overall appointment/scheduling system 200 as described above in a flow chart. The system receives the request 202 via API 203, data upload 203A, or manual entry 203B, with any combination of certain data constraints 205. The system then creates a route for appointment deliveries 204, utilizing a routing methodology 207 utilizing the constraints, particularly generating scores of routes for comparison purposes, and ultimately determines the best scored route(s) in relation thereto. The system then generates options 206 for client/patients (a multiple option 208 is the same as for the other alternative; a single option in terms of appointment time and date 210 is utilized with this alternative appointment scheduling system). Such a single option 210 is thus based upon the route generated 204 for transportation purposes. The system then updates 212 as more requests are received for the same appointment customer and/or date and time of appointment (or other data constraints 205) that may alter the route 204. Typically, though, upon the initial threshold of requests 202 to set the route 204, such will generate the route and thus appointments 210 for the requesting appointment clients/patients. Once the cutoff time 214 is met for such appointments and transportation routing, the completed schedule 216 is generated in relation to the data constraints 205 and the same is then communicated from the system to each appointment client/patient (and appointment customer) 218 with an estimated time of arrival and appointment date and time provided. or noroute optimization algorithm as described above in a flow chart.

In this way, as described above, the delivery client is provided an efficient route to optimize its own operations in multiple ways while providing each customer a suitable way to narrow down delivery times upon request, thus providing benefits to both parties within each transaction. Such a result has heretofore been nonexistent within the goods and/or service provider delivery industries. Additionally, the ability to structure an appointment scheduling/transportation providing system is provided through this disclosure, as well. Again, such has heretofore been unexplored within this field of endeavor.

Having described the invention in detail it is obvious that one skilled in the art will be able to make variations and modifications thereto without departing from the scope of the present invention. Accordingly, the scope of the present invention should be determined only by the claims appended hereto.

What we claim is:

1. A computer-implemented method for scheduling an appointment for a transportation service and generating a route to provide transportation for the transportation service, comprising:

receiving one or more requests for the transportation service from a plurality of users, wherein the one or more requests include data constraint, and wherein the data constraint includes location information, preferred date and time information, service type information, product information, contextual information, or a combination thereof;

generating a plurality of routes from locations of one or more service providers to locations of the plurality of users based, at least in part, on the one or more requests;

assigning scores to the plurality of routes based, at least in part, on the data constraint;

comparing the scores of the plurality of routes to determine at least one suitable route data for the transportation service to the plurality of users;

transmitting at least one transportation time window to the plurality of users based, at least in part, on the at least one suitable route data, wherein the at least one transportation time window includes multiple transportation time windows or a single transportation time window;
updating the plurality of routes based, at least in part, on one or more responses from the plurality of users within a pre-determined time threshold;
determining a final route based, at least in part, on the updated plurality of routes; and
transmitting the final route and estimated time of arrival to the plurality of users, the one or more service providers, or a combination thereof.

2. The computer-implemented method of claim 1, wherein generating the plurality of routes further comprises:
   determining whether the one or more requests for the transportation service from the plurality of users satisfy a minimum threshold for generating the plurality of routes; and
   upon determining the one or more requests from the plurality of users satisfy the minimum threshold:
      generating the plurality of routes further based on capability information, efficiency information, or a combination thereof of the one or more service providers, or
   upon determining the one or more requests from the plurality of users do not satisfy the minimum threshold:
      generating a presentation in at least one user interface of one or more devices associated with the plurality of users to request additional information pertaining to the transportation service until the minimum threshold is satisfied; and
      generating the plurality of routes upon determining the minimum threshold is satisfied.

3. The computer-implemented method of claim 1, wherein generating the plurality of routes further comprises:
   determining the plurality of users satisfies a minimum count threshold within a geographical region, and wherein the minimum count threshold is satisfied within the pre-determined time threshold.

4. The computer-implemented method of claim 1, wherein generating the plurality of routes further comprises:
   correlating, via a geo-location server, the one or more requests from the plurality of users with one or more locations within a geographical region to generate location coordinates, wherein the geo-location server stores the location information of the plurality of users.

5. The computer-implemented method of claim 1, further comprising:
   updating the assigned scores to the plurality of routes based, at least in part, on the one or more responses from the plurality of users within the pre-determined time threshold, profile information of the plurality of routes, or a combination thereof; and
   comparing the updated scores of the plurality of routes to determine the at least one suitable route data for the transportation service.

6. The computer-implemented method of claim 1, further comprising:
   upon determining the at least one transportation time window is the multiple transportation time windows:
      transmitting the transportation time windows from a list of available transportation time windows to the plurality of users based, at least in part, on the suitable route data; and
      updating the data constraint based, at least in part, on the responses from the plurality of users, or
   upon determining the at least one transportation time window is the single transportation time window:
      transmitting a transportation time window to the plurality of users based, at least in part, on the suitable route data; and
      updating the data constraint based, at least in part, on the responses from the plurality of users.

7. The computer-implemented method of claim 1, wherein generating the plurality of routes is further based, at least in part, on a total travel distance to complete the transportation service, an average travel distance between each transportation service locations, a total travel time to complete the transportation service, an average time at each transportation service locations, an average speed in the plurality of routes, a total number of vehicles available for the transportation service within the transportation time window, or a combination thereof.

8. The computer-implemented method of claim 1, further comprising:
   assigning one or more transportation time windows to the plurality of users based, at least in part, on time of response, wherein at least one user that responds earlier than other users is prioritized in allocation of the transportation time windows, and wherein the other users are assigned vacant transportation time windows around the assigned transportation time windows.

9. The computer-implemented method of claim 8, further comprising:
   determining the one or more responses from the plurality of users includes a request for rescheduling the transportation time window; and
   updating the transportation time window, the plurality of routes, or a combination thereof based, at least in part, on the request for rescheduling the transportation time window.

10. A system for scheduling an appointment for a transportation service and generating a route to provide transportation for the transportation service, comprising:
    one or more processors;
    a data storage storing instructions which, when executed by the one or more processors, cause the one or more processors to perform operations comprising:
       receiving one or more requests for the transportation service from a plurality of users, wherein the one or more requests include data constraint, and wherein the data constraint includes location information, preferred date and time information, service type information, product information, contextual information, or a combination thereof;
       generating a plurality of routes from locations of one or more service providers to locations of the plurality of users based, at least in part, on the one or more requests;
       assigning scores to the plurality of routes based, at least in part, on the data constraint;
       comparing the scores of the plurality of routes to determine at least one suitable route data for the transportation service to the plurality of users;
       transmitting at least one transportation time window to the plurality of users based, at least in part, on the at least one suitable route data, wherein the at least one transportation time window includes multiple transportation time windows or a single transportation time window;
       updating the plurality of routes based, at least in part, on one or more responses from the plurality of users within a pre-determined time threshold;
       determining a final route based, at least in part, on the updated plurality of routes; and transmitting the final route and estimated time of arrival to the plurality of users, the one or more service providers, or a combination thereof.

11. The system of claim 10, wherein generating the plurality of routes further comprises:
determining whether the one or more requests for the transportation service from the plurality of users satisfy a minimum threshold for generating the plurality of routes; and
upon determining the one or more requests from the plurality of users satisfy the minimum threshold:
generating the plurality of routes further based on capability information, efficiency information, or a combination thereof of the one or more service providers, or
upon determining the one or more requests from the plurality of users do not satisfy the minimum threshold:
generating a presentation in at least one user interface of one or more devices associated with the plurality of users to request additional information pertaining to the transportation service until the minimum threshold is satisfied; and
generating the plurality of routes upon determining the minimum threshold is satisfied.

12. The system of claim 10, wherein generating the plurality of routes further comprises:
determining the plurality of users satisfies a minimum count threshold within a geographical region, and wherein the minimum count threshold is satisfied within the pre-determined time threshold.

13. The system of claim 10, wherein generating the plurality of routes further comprises:
correlating, via a geo-location server, the one or more requests from the plurality of users with one or more locations within a geographical region to generate location coordinates, wherein the geo-location server stores the location information of the plurality of users.

14. The system of claim 10, the operations further comprising:
updating the assigned scores to the plurality of routes based, at least in part, on the one or more responses from the plurality of users within the pre-determined time threshold, profile information of the plurality of routes, or a combination thereof; and
comparing the updated scores of the plurality of routes to determine the at least one suitable route data for the transportation service.

15. The system of claim 10, the operations further comprising:
upon determining the at least one transportation time window is the multiple transportation time windows:
transmitting the transportation time windows from a list of available transportation time windows to the plurality of users based, at least in part, on the suitable route data; and
updating the data constraint based, at least in part, on the responses from the plurality of users, or
upon determining the at least one transportation time window is the single transportation time window:
transmitting a transportation time window to the plurality of users based, at least in part, on the suitable route data; and
updating the data constraint based, at least in part, on the responses from the plurality of users.

16. The system of claim 10, wherein generating the plurality of routes is further based, at least in part, on a total travel distance to complete the transportation service, an average travel distance between each transportation service locations, a total travel time to complete the transportation service, an average time at each transportation service locations, an average speed in the plurality of routes, a total number of vehicles available for the transportation service within the transportation time window, or a combination thereof.

17. A non-transitory machine-readable medium storing instructions that, when executed by a server, cause the server to perform operations for scheduling an appointment for a transportation service and generating a route to provide transportation for the transportation service, the operations comprising:
receiving one or more requests for the transportation service from a plurality of users, wherein the one or more requests include data constraint, and wherein the data constraint includes location information, preferred date and time information, service type information, product information, contextual information, or a combination thereof;
generating a plurality of routes from locations of one or more service providers to locations of the plurality of users based, at least in part, on the one or more requests;
assigning scores to the plurality of routes based, at least in part, on the data constraint;
comparing the scores of the plurality of routes to determine at least one suitable route data for the transportation service to the plurality of users;
transmitting at least one transportation time window to the plurality of users based, at least in part, on the at least one suitable route data, wherein the at least one transportation time window includes multiple transportation time windows or a single transportation time window;
updating the plurality of routes based, at least in part, on one or more responses from the plurality of users within a pre-determined time threshold;
determining a final route based, at least in part, on the updated plurality of routes; and
transmitting the final route and estimated time of arrival to the plurality of users, the one or more service providers, or a combination thereof.

18. The non-transitory machine readable medium of claim 17, wherein generating the plurality of routes further comprises:
determining whether the one or more requests for the transportation service from the plurality of users satisfy a minimum threshold for generating the plurality of routes; and
upon determining the one or more requests from the plurality of users satisfy the minimum threshold:
generating the plurality of routes further based on capability information, efficiency information, or a combination thereof of the one or more service providers, or
upon determining the one or more requests from the plurality of users do not satisfy the minimum threshold:
generating a presentation in at least one user interface of one or more devices associated with the plurality of users to request additional information pertaining to the transportation service until the minimum threshold is satisfied; and
generating the plurality of routes upon determining the minimum threshold is satisfied.

19. The non-transitory machine readable medium of claim 17, wherein generating the plurality of routes further comprises:
 determining the plurality of users satisfies a minimum count threshold within a geographical region, and wherein the minimum count threshold is satisfied within the pre-determined time threshold.

20. The non-transitory machine readable medium of claim 17, wherein generating the plurality of routes further comprises:
 correlating, via a geo-location server, the one or more requests from the plurality of users with one or more locations within a geographical region to generate location coordinates, wherein the geo-location server stores the location information of the plurality of users.

* * * * *